(12) United States Patent
Pokrovski et al.

(10) Patent No.: US 9,650,320 B2
(45) Date of Patent: *May 16, 2017

(54) HIGH TEMPERATURE ISOMERIZATION OF (E)-1-CHLORO-3,3,3-TRIFLUOROPROPENE TO (Z)-1-CHLORO-3,3,3-TRIFLUOROPROPENE

(71) Applicant: HONEYWELL INTERNATIONAL INC., Morristown, NJ (US)

(72) Inventors: Konstantin A. Pokrovski, Orchard Park, NY (US); Daniel C. Merkel, Orchard Park, NY (US); Hsueh S. Tung, Getzville, NY (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/886,628

(22) Filed: Oct. 19, 2015

(65) Prior Publication Data

US 2016/0185692 A1    Jun. 30, 2016

Related U.S. Application Data

(62) Division of application No. 14/204,637, filed on Mar. 11, 2014, now Pat. No. 9,162,947.

(60) Provisional application No. 61/789,312, filed on Mar. 15, 2013.

(51) Int. Cl.
   *C07C 17/358*    (2006.01)

(52) U.S. Cl.
   CPC ........ *C07C 17/358* (2013.01); *C07B 2200/09* (2013.01)

(58) Field of Classification Search
   CPC .................................................. C07C 17/358
   See application file for complete search history.

(56) References Cited

U.S. PATENT DOCUMENTS

| | | | |
|---|---|---|---|
| 9,162,947 B2 * | 10/2015 | Pokrovski | C07C 17/358 |
| 2010/0152504 A1 * | 6/2010 | Hulse | C07C 17/358 |
| | | | 570/151 |
| 2014/0275644 A1 * | 9/2014 | Merkel | C07C 17/383 |
| | | | 570/151 |

* cited by examiner

*Primary Examiner* — Jafar Parsa
*Assistant Examiner* — Medhanit Bahta
(74) *Attorney, Agent, or Firm* — Bruce O. Bradford

(57) ABSTRACT

Disclosed are processes for a high temperature isomerization reaction converting (E)-1-chloro-3,3,3-trifluoropropene to (Z)-1-chloro-3,3,3-trifluoropropene. In certain aspects of the invention, such a process includes contacting a feed stream with a heated surface, where the feed stream includes (E)-1-chloro-3,3,3-trifluoropropene or mixture of (E)-1-chloro-3,3,3-trifluoropropene with (Z)-1-chloro-3,3,3-trifluoropropene. The resulting product stream includes (Z)-1-chloro-3,3,3-trifluoropropene and (E)-1-chloro-3,3,3-trifluoropropene, where the ratio of (Z) isomer to (E) isomer in the product stream is higher than the ratio feed stream. The (E) and (Z) isomers in the product stream may be separated from one another.

18 Claims, No Drawings

HIGH TEMPERATURE ISOMERIZATION OF (E)-1-CHLORO-3,3,3-TRIFLUOROPROPENE TO (Z)-1-CHLORO-3,3,3-TRIFLUOROPROPENE

CROSS REFERENCE TO RELATED APPLICATIONS

The present application is a division of U.S. application Ser. No. 14/204,637, filed Mar. 11, 2014, which application claims priority to U.S. Provisional Application Ser. No. 61/789,312, filed Mar. 15, 2013, the contents of which are incorporated herein by reference in their entirety.

FIELD OF THE INVENTION

The present invention relates to processes for the production of 1-chloro-3,3,3-trifluoropropene (1233zd) and, in certain aspects, to the conversion of a 1-chloro-3,3,3-trifluoropropene (E) isomer to a 1-chloro-3,3,3-trifluoropropene (Z) isomer.

BACKGROUND

Many existing CFCs are known to be ozone-depleting compounds. Thus, the use of these compounds has been curtailed in favor of chemicals that are more commercially acceptable. In some cases, alternate CFC compounds have been found to be both effective and more environmentally friendly. As one example, 1-chloro-3,3,3-trifluoropropene (hereinafter "1233zd") has been found to have a wide variety of uses, for example as a heat transfer agent, as a foaming agent, and as a solvent, among other uses. U.S. Patent Publication Nos. 2008/0098755, entitled "Heat Transfer Methods Using Heat Transfer Compositions Containing Trifluoromonochloropropene," and 2008/0207788, entitled "Foaming Agents, Foamable Compositions, Foams and Articles Containing Fluorine Substituted Halogens, and Methods of Making the Same" and U.S. Pat. No. 6,362,383, entitled "Hydro-Fluorination of Chlorinated Hydrocarbons" all disclose examples of such uses. The contents of each of these references are incorporated herein by reference in their entirety.

1233zd may be produced by any one of a number of different methods. For example, U.S. Pat. No. 7,829,747, entitled "Process for Dehydrofluorination of 3-chloro-1,1,13-tetrafluoropropane to 1-chloro-3,3,3-trifluoropropene"; U.S. Pat. No. 5,710,352, entitled "Vapor Phase Process for Making 1,1,1,3,3-pentafluoropropane and 1-chloro-3,3,3-trifluoropropene;" U.S. Pat. No. 6,111,150, entitled "Method for Producing 1,1,1,3,3-pentafluoropropane;" and U.S. Pat. No. 6,844,475, entitled "Low Temperature Production of 1-chloro-3,3,3-trifluoropropene (HCFC-1233zd)" all describe several methods for making 1233zd. The contents of each of these references incorporated by reference herein in their entirety.

1233zd has two isomers, (E) and (Z), with different physical properties. As one example of the different properties between the two isomers, 1233zd(Z) has a boiling point of approximately 38° C., whereas 1233zd(E) has a boiling point of approximately 19° C. In some applications, it is desirable to use either pure 1233zd(E), pure 1233zd(Z), a particular blend of the (Z) and (E) isomers, or a particular blend of one or both of the 1233zd isomers and another compound in order to control the properties of the solution. For example, in some solvent applications, it is desirable to have a relatively high boiling point. In some such applications, pure 1233zd(Z) may have more desirable physical properties (e.g., a higher boiling point) than either pure 1233zd(E) or mixtures of the two 1233zd isomers.

In some prior art isomerization reactions, reagents (defined herein as any chemically reactive materials, i.e., not the 1233zd itself or the various catalysts described herein) are used to facilitate the isomerization of the 1233zd. For example, in one prior art isomerization reaction bromine is added to 1233zd(E) in order to isomerize 1233zd. In some embodiments of the present invention, the isomerization reaction is reagent-free, or it does not require the use of any reagents. As further described below, in some embodiments the absence of reagents facilitates the production of pure 1233zd, and more particularly may facilitate the production of pure 1233zd(Z) and pure 1233zd(E).

Isomerization of 1233zd(E) to form 1233zd(Z) is disclosed in the U.S. Pat. No. 8,217,208, the contents of which are incorporated herein by reference in its entirety, which provides a low temperature isomerization process. The deficiency of this process, however, is that it results in low selectivity to 1233zd(Z) and the formation of significant amounts of by-products (see, for example, table 3 of example 4 exhibiting selectivity to 1233zd(Z) of about 80%).

Accordingly, there exists a need for processes that selectively provide one or both of the commercially desirable isomers of 1233zd, particularly for the conversion of 1233zd (E) to form 1233zd(Z) with increased yield and selectivity.

SUMMARY

The present invention, in certain aspects, relates to a high temperature process for converting a 1233zd(E) isomer to a 1233zd(Z) isomer. In certain preferred aspects, such a method includes providing a feed stream comprising, consisting essentially of, or consisting of (E)1-chloro-3,3,3-trifluoropropene or a mixture of (E)1-chloro-3,3,3-trifluoropropene and (Z)1-chloro-3,3,3-trifluoropropene. In further aspects, the latter mixture of the (E) and (Z) isomers contains less than about 5 wt % (Z)1-chloro-3,3,3-trifluoropropene, based on the total weight of the feed stream.

The feed stream is contacted with a heated surface that is maintained at a temperature of greater than 400° C. for a period of time sufficient to convert at least a portion of the (E) 1-chloro-3,3,3-trifluoropropene to (Z)1-chloro-3,3,3-trifluoropropene. To this end, it results in a product stream having more (Z) isomer than in the feed stream. In certain aspects, the heated surface is maintained at a temperature from greater than 400° C. to about 550° C., in further embodiments from greater than 400° C. to about 500° C., in even further embodiments from greater than 400° C. to about 475° C., and in even further embodiments from greater than 400° C. to about 450° C. The feed stream may be optionally vaporized before or after contacting the heated surface.

The heated surface may also include an outer packing material, which in certain aspects acts as a catalyst to the reaction. Non-limiting examples of such packing material include stainless steel, nickel and nickel-based compositions. In certain embodiments, they include nickel-based alloys. Other catalysts may include, but are not limited to, metal oxides, halogenated metal oxides, Lewis acid metal halides, zero-valent metals, or a mixture or alloy thereof.

The resulting product stream may be distilled to separate the (E) and (Z) isomers from one another. In certain aspects, the product stream contains more than 5 wt % (Z)1-chloro-3,3,3-trifluoropropene, based on the total weight of the product stream. In further embodiments, it contains between about 5 wt % and about 17 wt % (Z)1-chloro-3,3,3-trifluoropropene, based on the total weight of the product stream.

Additional embodiments and advantages of the instant invention will be readily apparent to one of skill in the art based on the additional disclosure provided herein.

DETAILED DESCRIPTION

The present invention relates, in part, to a high temperature process for isomerization of 1233zd(E) to form 1233zd(Z). Applicants to the present invention have surprisingly and unexpectedly found the high temperature process described herein results in improved conversion of the 1233zd(E) isomer and improved selectivity for the 1233zd(Z) isomer. In certain aspects, the selectivity for 1233zd(Z) is greater than 80%, greater than 90%, or greater than 95%.

As further described below, in certain embodiments of the present invention the feed stream comprises, consists essentially of, or consists of either 1233zd(E) or a mixture of 1233zd(E) and 1233zd(Z). The feed stream also may contain materials or impurities other than 1233zd(Z) or 1233zd(E). In certain non-limiting embodiments, the feed streams may be substantially free of such impurities. To this end, and in certain non-limiting embodiments, substantially free (at least with respect to the impurities) means that the impurity level is sufficiently low such that the impurities do not measurably impact the isomerization process provided herein. In further non-limiting embodiments, the feed streams may also be substantially free of impurities if they contain less than 5 wt %, less than 3 wt %, less than 2 wt %, less than 1.5 wt %, or less than 1 wt % of other compounds, based on the total weight of the feed stream. Non-limiting examples of such impurities may include hydrofluorocarbons, hydrochlorocarbons, hydrochlorofluorocarbons, halogenated olefins, or other compounds other than 1233zd. Some of these compounds may be byproducts or unreacted compounds from the production of the 1233zd. While it is preferred in certain embodiments that the impurities not react or interfere with isomerization process, in certain other embodiments, the impurities or additional materials, if present, may react with the 1233zd or with other compounds within an isomerization reaction, and in the process may affect the yield or purity of a product stream from the isomerization reaction.

According to certain embodiments of the invention, a method is provided for converting between the (E) and (Z) isomers of 1233zd, particularly to conversion the (E) isomer to the (Z) isomer. The method includes an isomerization reaction that has a thermodynamic equilibrium at which an equilibrium ratio of (E) isomer to (Z) isomer is present. As indicated by the examples described below, the equilibrium ratio may vary depending on certain reaction conditions, including the temperature, the type and configuration of the reactor vessel, and/or the presence of one or more catalysts. If the ratio of E to Z isomer is greater than the equilibrium ratio, then at least a portion of the 1233zd(E) is converted into 1233zd(Z).

In other embodiments, the method includes controlling the temperature of a heated surface to greater than 300° C., in certain preferred aspects to greater than 350° C., and in further preferred aspects to greater than 400° C. The heated surface is contacted with a feed stream comprising, consisting essentially of, or consisting of 1233zd(E) or a mixture of (E) and 1233zd(Z). This contacting step may be for any period of time sufficient to convert at least a portion of the 1233zd(E) to 1233zd(Z), thus producing a product stream with a concentration of 1233zd(Z) that is higher than that in the feed stream.

In certain embodiments, the heated surface includes the interior surface of a reactor vessel. In addition, or in the alternative, the heated surface may include an outer surface of a packing material, for example a packing material that is packed in a reaction vessel. In certain embodiments, the reactor vessel is a continuous-type reactor vessel, for example a reactor vessel is a plug flow reactor. The feed stream is fed into the reactor vessel at a rate sufficient to isomerize the desired amount of 1233zd(E) to 1233zd(Z). The resulting product stream exits the reactor and is available for further purification of E and Z isomers of 1233zd. In one example, the reactor vessel is an elongate reactor vessel (e.g., a Stainless Steel, nickel Inconel, or Monel tube or pipe).

In certain embodiments, the reactor vessel may be partially or entirely packed with packing material, for example with a stainless steel packing, nickel packing, inconel packing, monel packing, or the like. In certain embodiments, the relatively large surface area of the packing material may facilitate the conversion reaction between the (E) and (Z) isomers. Support structures that support the packing material may also be disposed in or on the reactor vessel. For example, the packing material may be supported by a mesh or other structure that is disposed under, around, and/or within the packing material. The support structure may comprise the same material as the packing material (e.g., stainless steel, nickel, inconel, monel), nickel, or any other suitable material.

The packing materials may also comprise one or more catalyst materials. Examples of suitable catalysts for the isomerization of 1233zd are zero-valent metals supported on a substrate (activated carbon, metal oxide, metal oxyhalide, metal halide) or unsupported, as well as combinations of these catalysts. In certain preferred aspects, the packing materials are adapted to increase selectivity and conversion at temperatures greater than 400° C. and may exhibit catalytic properties. Non-limiting examples of such packing materials include stainless steel, nickel and nickel-containing compositions. In certain preferred aspects, the packing materials include nickel-based alloys. Non-limiting examples of such nickel-based alloys include, but not limited to, Monel® based materials (including Monel® 400) and Inconel® based materials (including Inconel® 600 and 625).

The feed stream may be fed into the reactor vessel in the vapor phase. Alternately, the feed stream is fed into the reactor vessel in the liquid phase and the temperature of the heated surface within the reactor vessel causes the feed stream to vaporize. Examples of suitable temperatures for the heated surface within the reactor vessel are greater than about 250° C., greater than about 300° C., greater than about 350° C., or greater than about 400° C. In certain embodiments, the temperature of the heated surface within the reaction vessel is from greater than 400° C. to about 550° C., from greater than 400° C. to about 500° C., from greater than 400° C. to about 475° C., or from greater than 400° C. to about 450° C.

The pressure in the reactor vessel during the isomerization reaction may be at or slightly above atmospheric pressure, or it may be between atmospheric pressure and 300 psi, between atmospheric pressure and 200 psi, or between atmospheric pressure and 100 psi. In continuous-type reactor vessels, the feed stream may be fed in at slightly above atmospheric pressure or within any of the elevated pressure ranges specified above, or the feed stream may be fed into the reactor vessel below atmospheric pressure and the exit of the reactor vessel may be placed under vacuum.

In certain embodiments, the feed steam includes a mixture of 1233zd(E) and 1233zd(Z). While the amount of 1233zd (Z) is not necessarily limiting to the present invention and such an isomer may be provided in any amount, in certain aspects, it is present in an amount of less than about 10 wt %, in further aspects in an amount less than 9 wt. % 1233zd(Z), and in further embodiments in an amount of less than about 7 wt. % of the composition, based on the total weight of the feed stream. In certain embodiments, feed stream is substantially free of 1233zd(Z), which includes compositions having no measurable amount of 1233zd(Z). In further non-limiting embodiments, however, the feed steam may be substantially free of 1233zd(Z) if it contains less than 5 wt % 1233zd(Z), less than 3 wt % 1233zd(Z), less than 1 wt. % 1233zd(Z), or is entirely free of 1233zd(Z), based on the total weight of the feed stream.

The feed stream in any of the foregoing amounts is then contacted with a heated surface, particularly within the temperature ranges provided herein for a sufficient or effective amount of time such that the desired amount of 1233zd (Z) is present in the product stream. In certain non-limiting aspects, a "sufficient time" or "effective time" means an amount of time where measurable conversion of 1233zd(E) to 1233zd(Z) is detectable or where the amount of 1233zd (Z) in the resulting product stream is within the desired range, particularly the weight percentage ranges provided herein. In certain further aspects of the invention such times may be between 1 second and 15 minutes, in certain preferred aspects between about 10 seconds and 5 minutes.

The amount of 1233zd(Z) in the product stream may be any amount greater than the concentration of 1233zd(Z) in the starting or feed stream. In certain embodiments, this amount is greater than 1%, greater than about 5 wt %, greater than about 7 wt %, greater than about 9 wt %, greater than about 10 wt %, greater than about 12 wt %, or greater than about 15 wt %, based on the total weight of the product stream. In further embodiments, the amount of 1233zd(Z) in the product stream may be between about 5 wt % and about 20 wt %, between about 5 wt % and about 17 wt %, between about 5 wt % and about 15 wt %, between about 5 wt % and about 12 wt %, or about 5 wt %, about 7 wt %, about 9 wt %, about 10 wt %, about 12 wt %, or about 15 wt %, based on the total weight of the product stream. In certain embodiments, the amount of 1233zd(Z) in the product stream corresponds to the equilibrium ratio of 1233zd(Z), whereas in other embodiments the amount of 1233zd(Z) corresponds to less than the equilibrium ratio of 1233zd(Z).

In further embodiments, the amount of 1233zd(E) in the product stream may be less than about 95 wt %, less than about 90 wt %, less than about 80 wt %, less than about 70 wt %, less than about 60 wt %, based on the total weight of the product stream.

In certain alternative embodiments of the invention, the method of converting between (E)1-chloro-3,3,3-trifluoropropene and (Z)1-chloro-3,3,3-trifluoropropene, comprises providing a vaporized feed stream comprising, consisting essentially of, or consisting of one or both isomers of 1-chloro-3,3,3-trifluoropropene. The feed stream has a first ratio of (E) isomer to (Z) isomer. As discussed herein, a temperature controlled reaction vessel may be used that includes an interior surface, a first opening, a second opening, a pathway fluidly connecting the first and second openings, and a packing material disposed in the pathway. The heated surface may include the interior surface and the packing material contacting the feed stream with the heated surface that is maintained at a desired temperature. The desired temperature may be any of the temperature ranges mentioned herein, in certain preferred embodiments greater than 350° C., in further preferred embodiments greater than 400° C., or as otherwise provided herein. The feed stream may be contacted with the heated surface for a period of time sufficient to convert the feed stream into a product stream having a second ratio of (E) to (Z) isomer.

Because the methods described above include equilibrium reactions, the product streams will comprise a mixture of both isomers of 1233zd. However, because of differing physical properties (e.g., different boiling points), the two isomers may be separated from one another using a separation process. For example, the product stream from any of the above methods may be fed directly into a suitable distillation operation. In other embodiments, the product stream is fed through an intermediate unit operation prior to being fed into the distillation column or is stored prior to being fed through the distillation column. In certain embodiments, the distillation process yields substantially pure, or pure, separated product streams of 1233zd(Z) and 1233zd (E). Where only one of the (Z) or (E) separated product streams are commercially desirable, all or a portion of the undesirable separated product stream may be recycled back into an isomerization process.

In certain embodiments in which the product streams of the above methods comprises additional compounds other than the isomers of 1233zd, the additional compounds may have similar properties (e.g., boiling points) to one of the (Z) or (E) isomers that may cause the additional compounds to be captured in either or both of the (Z) or (E) product streams. In such embodiments, the (Z) or (E) product stream(s) with the additional compounds may be useful for particular applications. In other embodiments, the product stream(s) with the additional compounds may be discarded, a portion of the product stream(s) with the additional compounds may be recycled into the feed stream for one of the isomerization methods, and/or a portion of the product stream(s) may be sent to an additional unit operation that will separate the 1233zd from one or all of the additional compounds. In other embodiments, the additional compounds may have properties that differ from both the 1233zd (Z) and the 1233zd(E), allowing the 1233zd(Z), the 1233zd (E) and the additional compounds to be separated into three or more product streams.

Further, in certain methods of producing 1233zd, the product stream includes both the (Z) and (E) isomers along with byproducts and unreacted materials. In certain such embodiments, a separation operation (e.g., a distillation operation) is used to separate the (Z) and (E) product streams from one another, but many of the byproducts and unreacted materials have boiling points and/or other properties that cause at least a portion of the byproducts and unreacted materials to be captured in one of the product streams, for example in the 1233zd(E) product stream. In such embodiments, the 1233zd(E) product stream may be captured for other uses, and the pure or substantially pure 1233zd(Z) product stream may be used as the feed stream for one of the isomerization methods described above in order to produce a product stream consisting essentially of a mixture of (E)

and 1233zd(Z). As described above, the product stream from the isomerization method may then be fed into a separation process in order to yield separate product streams for the (Z) and (E) isomers.

In certain embodiments, a 1233zd production operation is connected directly or indirectly with a first separation operation to separate the (Z) isomer, the (E) isomer and the byproducts and unreacted materials. The first separation operation may be directly or indirectly connected with an isomerization operation, which in turn may be directly or indirectly connected with a second separation operation. As used herein, "indirectly connected" includes both being connected via another unit operation as well as embodiments in which the product stream is stored for a time prior to being fed to the next operation.

EXAMPLES

The following examples are provided for the purpose of illustrating the present invention but without limiting the scope thereof.

Example 1

99.9% pure 1233zd(E) was fed into Inconel 625 reactor packed with Inconel 625 mesh (ID=¾ inch, L=31 inch) at the rate of 15 g/hr. The reactor was equipped with a multi point thermocouple positioned in the center of the reactor and a vaporizer installed at the inlet of the reactor. The isomerization reaction was carried out at the reaction temperatures between 355 and 449° C. The reaction products were sampled and analyzed by GC. The results are presented in Table 1 below.

TABLE 1

1233zd(E) isomerization results in Inconel 625 with Inconel 625 mesh

| Reaction Temp (° C.) | 1233zd(E) (%) | 1233zd(Z) (%) | selectivity to 1233zd(Z) (%) | Conversion of 1233zd(E) (%) |
|---|---|---|---|---|
| 355 | 98.002 | 1.886 | 94.42% | 2.00% |
| 400 | 96.600 | 3.286 | 96.65% | 3.40% |
| 449 | 87.971 | 11.685 | 97.15% | 12.03% |

Example 2

99.9% pure 1233zd(E) was fed into empty Inconel 625 reactor (ID=¾ in, L=31 in) at the rate of 15 g/hr. The reactor was equipped with a multi point thermocouple positioned in the center of the reactor and a vaporizer installed at the inlet of the reactor. The isomerization reaction was carried out at the reaction temperatures between 400 and 450° C. The reaction products were sampled and analyzed by GC. The results are presented in Table 2 below.

TABLE 2

1233zd(E) isomerization in empty Inconel 625 reactor

| Reaction Temp (° C.) | 1233zd(E) (%) | 1233zd(Z) (%) | selectivity to 1233zd(Z) (%) | Conversion of 1233zd(E) (%) |
|---|---|---|---|---|
| 400 | 96.723 | 3.113 | 94.98% | 3.28% |
| 450 | 88.328 | 11.271 | 96.56% | 11.67% |

Example 3

99.9% pure 1233zd(E) was fed into Monel 400 reactor packed with Monel 400 mesh (ID=¾ inch, L=31 inch) at the rate of 15 g/hr. The reactor was equipped with a multi point thermocouple positioned in the center of the reactor and a vaporizer installed at the inlet of the reactor. The isomerization reaction was carried out at the reaction temperatures of 400° C. and 450° C. The reaction products were sampled and analyzed by GC. The results are presented in Table 3 below.

TABLE 3

1233zd(E) isomerization in Monel 400 reactor packed with Monel 400 mesh

| Reaction Temp (° C.) | 1233zd(E) (%) | 1233zd(Z) (%) | selectivity to 1233zd(Z) (%) | Conversion of 1233zd(E) (%) |
|---|---|---|---|---|
| 400 | 95.359 | 4.514 | 97.27% | 4.64% |
| 450 | 87.778 | 11.812 | 96.65% | 12.22% |

Example 4

99.9% pure 1233zd(E) was fed into Inconel 625 reactor packed with Stainless Steel packing (ID=¾ inch, L=31 inch, packing size 0.25 in) at the rate of 15 g/hr. The reactor was equipped with a multi point thermocouple positioned in the center of the reactor and a vaporizer installed at the inlet of the reactor. The isomerization reaction was carried out at the reaction temperatures between 400 and 450° C. The reaction products were sampled and analyzed by GC. The results are presented in Table 4 below.

TABLE 4

1233zd(E) isomerization in Inconel 625 reactor packed with Stainless Steel packing

| Reaction Temp (° C.) | 1233zd(E) (%) | 1233zd(Z) (%) | selectivity to 1233zd(Z) (%) | Conversion of 1233zd(E) (%) |
|---|---|---|---|---|
| 400 | 88.788 | 10.961 | 97.76% | 11.21% |
| 425 | 85.089 | 14.441 | 96.85% | 14.91% |
| 450 | 85.239 | 14.076 | 95.36% | 14.76% |

Comparative Example 1

Conversion of 1233zd(E) into 1233zd(Z) was performed using a Inconel 625 reactor (ID ¾ inch, length 31 inch) equipped with a vaporizer. The reactor was filled with 40 mL of pelletized fluorinated crystalline $Cr_2O_3$ catalyst positioned in the middle portion of the reactor. Nickel mesh was placed at the top and at the bottom of reactor to support the catalyst. A multi-point thermocouple was inserted at the center of the reactor. 99.9% pure 1233zd(E) was introduced into the reactor at the rate of 15 g/hr. The reactor temperature for this experiment was controlled in the range 225-400° C. The temperature gradient throughout the reactor never exceeded 3-5° C. Samples of reaction products were taken every hour and GC analysis of those samples is given in Table 5 below.

TABLE 5

| Reaction Temperature (° C.) | 1233zd(E) (%) | 1233zd(Z) (%) | selectivity to 1233zd(Z) (%) | Conversion of 1233zd(E) (%) |
|---|---|---|---|---|
| 225 | 90.292 | 8.625 | 88.84 | 9.71 |
| 250 | 89.851 | 8.830 | 87.00 | 10.15 |
| 275 | 89.127 | 9.272 | 85.28 | 10.87 |
| 300 | 88.317 | 9.692 | 82.96 | 11.68 |
| 350 | 85.932 | 10.941 | 77.78 | 14.07 |
| 400 | 84.614 | 11.708 | 76.10 | 15.39 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. In the foregoing, all temperatures are set forth uncorrected in degrees Celsius and, all parts and percentages are by weight, unless otherwise indicated.

From the foregoing description, one skilled in the art can ascertain the essential characteristics of this invention and, without departing from the spirit and scope thereof, can make various changes and modifications of the invention to adapt it to various usages and conditions.

What is claimed is:

1. A method of converting (E)1-chloro-3,3,3-trifluoropropene into (Z)1-chloro-3,3,3-trifluoropropene, comprising:
   providing a reaction mixture comprising (E)1-chloro-3,3,3-trifluoropropene and, optionally, (Z)-1-chloro-3,3,3-trifluoropropene;
   heating said reaction mixture to temperature of greater than 400° C. for a period of time and under conditions effective to form a product mixture comprising a concentration of (Z)1-chloro-3,3,3-trifluoropropene that is greater than that provided in the reaction mixture.

2. The method of claim 1, wherein said reaction mixture is heated to a temperature from greater than 400° C. to about 550° C.

3. The method of claim 1, wherein said reaction mixture is heated to a temperature from greater than 400° C. to about 500° C.

4. The method of claim 1, wherein said reaction mixture is heated to a temperature from greater than 400° C. to about 475° C.

5. The method of claim 1, wherein said reaction mixture is heated to a temperature from greater than 400° C. to about 450° C.

6. The method of claim 1, further comprising the step of providing a temperature controlled reaction vessel that includes an interior surface, a first opening, a second opening, a pathway fluidly connecting the first and second openings, and a packing material disposed in the pathway.

7. The method of claim 1, further comprising vaporizing the reaction mixture before the heating step.

8. The method of claim 1, further comprising vaporizing the reaction mixture during the heating step.

9. The method of claim 1, wherein the reaction mixture comprises (E)1-chloro-3,3,3-trifluoropropene and (Z)1-chloro-3,3,3-trifluoropropene.

10. The method of claim 9, wherein the (Z)1-chloro-3,3,3-trifluoropropene is provided in the reaction mixture in an amount of less than 5 wt. %, based on the total weight of the reaction mixture.

11. The method of claim 1, wherein sufficient (E)1-chloro-3,3,3-trifluoropropene is converted to (Z)1-chloro-3,3,3-trifluoropropene to yield a product mixture having more than 5 wt % (Z)1-chloro-3,3,3-trifluoropropene, based on the total weight of the product mixture.

12. The method of claim 1, wherein the product mixture has between about 5 wt % and about 20 wt % (Z)-1-chloro-3,3,3-trifluoropropene, based on the total weight of the product mixture.

13. The method of claim 6, wherein at least a portion of the reaction mixture is heated by an outer surface of the packing material.

14. The method of claim 13, wherein the packing material has catalytic properties.

15. The method of claim 14, wherein the packing material comprises a stainless steel, nickel or nickel-based composition.

16. The method of claim 14, wherein the packing material comprises a nickel-based alloy.

17. The method of claim 1, wherein the product mixture consists essentially of (E)-1-chloro-3,3,3-trifluoropropene and (Z)1-chloro-3,3,3-trifluoropropene.

18. The method of claim 1, wherein the method of converting is reagent-free.

* * * * *